(12) United States Patent
Wedeen

(10) Patent No.: US 6,614,226 B2
(45) Date of Patent: Sep. 2, 2003

(54) DIFFUSION IMAGING OF TISSUES

(75) Inventor: Van Wedeen, Somerville, MA (US)

(73) Assignee: The General Hospital Corporation, Boston, MA (US)

(*) Notice: Subject to any disclaimer, the term of this patent is extended or adjusted under 35 U.S.C. 154(b) by 57 days.

(21) Appl. No.: 09/825,469

(22) Filed: Apr. 2, 2001

(65) Prior Publication Data

US 2002/0042569 A1 Apr. 11, 2002

Related U.S. Application Data

(60) Provisional application No. 60/193,938, filed on Mar. 31, 2000.

(51) Int. Cl.[7] .................................................. G01V 3/00
(52) U.S. Cl. ...................................... 324/309; 324/307
(58) Field of Search ............................... 324/307, 309, 324/303, 306, 312, 314, 318, 320, 322; 600/410

(56) References Cited

U.S. PATENT DOCUMENTS

| | | | |
|---|---|---|---|
| RE33,391 E | 10/1990 | Breton et al. | 324/309 |
| 5,428,291 A | 6/1995 | Thomann et al. | 324/303 |
| 5,539,310 A | 7/1996 | Basser et al. | 324/307 |
| 5,642,047 A * | 6/1997 | Bernatein | 324/309 |
| 6,150,814 A * | 11/2000 | Redpath et al. | 324/307 |

* cited by examiner

Primary Examiner—Edward Lefkowitz
Assistant Examiner—Brij B. Shrivastav
(74) Attorney, Agent, or Firm—Fish & Richardson P.C.

(57) ABSTRACT

The invention relates to the use of diffusion spectrum magnetic resonance imaging (MRI) to map complex fiber architectures in tissues. The new methods can be used to resolve intravoxel heterogeneity of diffusion in vivo with MRI of diffusion density spectra.

43 Claims, 15 Drawing Sheets

(9 of 15 Drawing Sheet(s) Filed in Color)

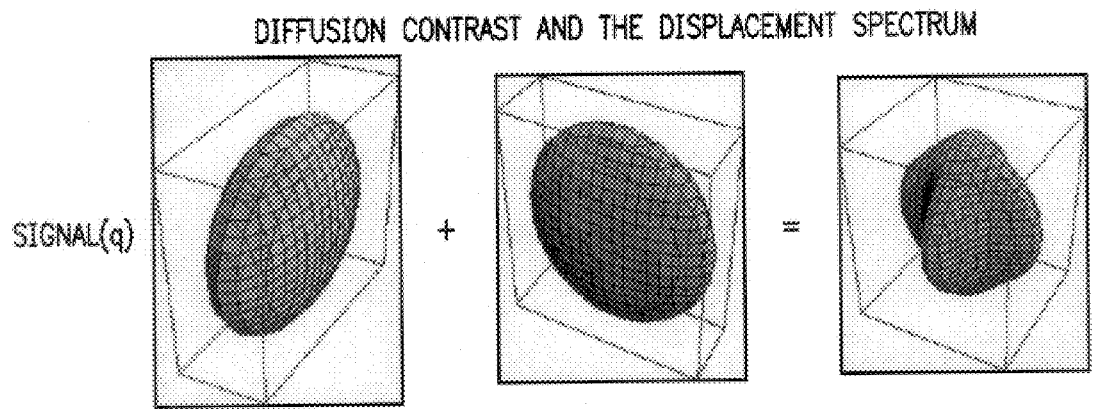

FIG. 1A

DIFFUSION CONTRAST AND THE DISPLACEMENT SPECTRUM

SIGNAL(q)

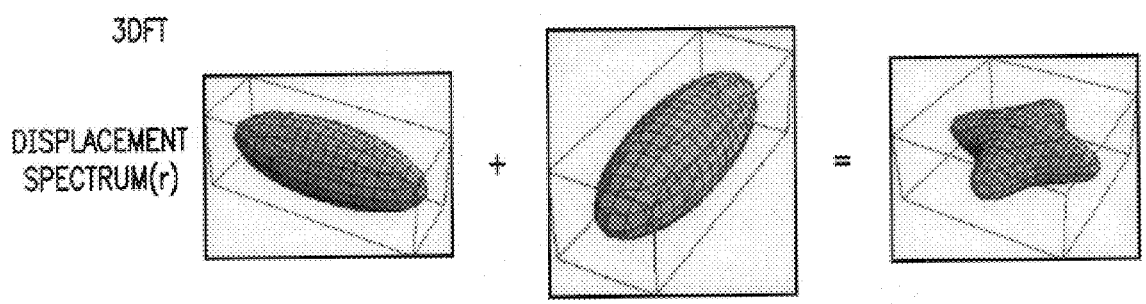

3DFT

DISPLACEMENT SPECTRUM(r)

FIG. 1B

DIFFUSION SPECTRUM MRI METHOD

- SINGLE-SHOT SPIN ECHO EPI
  EXTRA 180'S "BALANCE" DIFFUSION-GRADIENT EDDY EFFECTS
  RESOLUTION $3^3 - 4^3$ mm3
  TE ≈ 160 ms

- PHASE-ENCODE DIFFUSION: ≈ 500 'BIPOLAR' GRADIENTS, A 3D LATTICE IN A SPHERICAL KEYHOLE $|q|_{MAX} \geq$ CONSTANT
  $b_{MAX} = 20000$ s mm$^{-2}$

- RECONSTRUCT THE DIFFUSION SPECTRUM AT EACH VOXEL AS THE 3DFT OF THE SIGNAL MODULUS $P(r) = \mathcal{F}|S(q)|$

FIG. 2

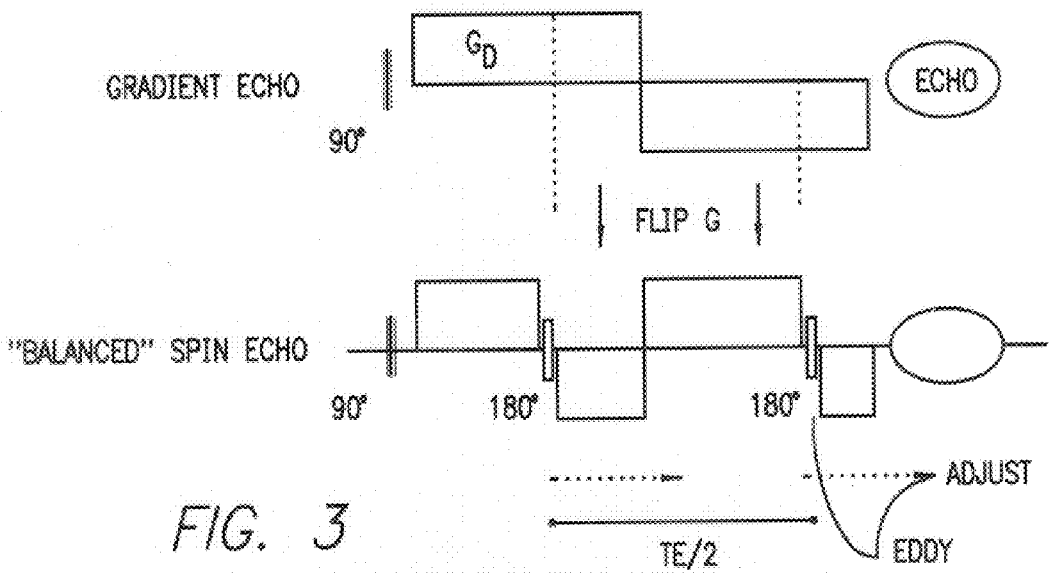
FIG. 3
"BALANCED" DIFFUSION PULSE SEQUENCE IS A SYMMETRIC SPIN ECHO THAT:
1) FILLS AVAILABLE TE WITH GRADIENTS
2) CANCELS RESIDUAL EDDY'S WITH + AND − GRADIENT TRANSITIONS
FIG. 4A EXAMPLE: DIFFUSION RESTRICTED IN A 1D BOX
TRANSPORT MATRICES $P_{ij}$ AT INCREASING $\tau^{1/2}$
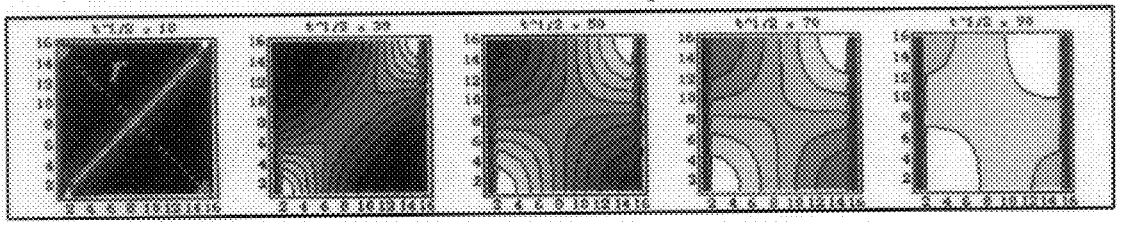
CORRESPONDING DISPLACEMENT SPECTRA AND THEIR FT'S
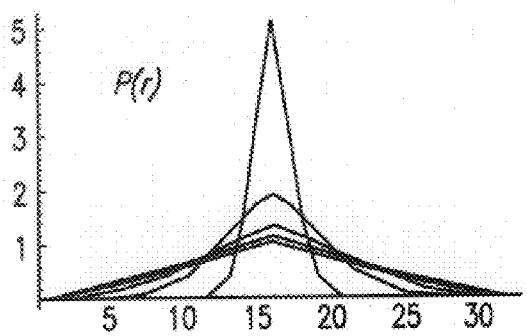
FIG. 4B
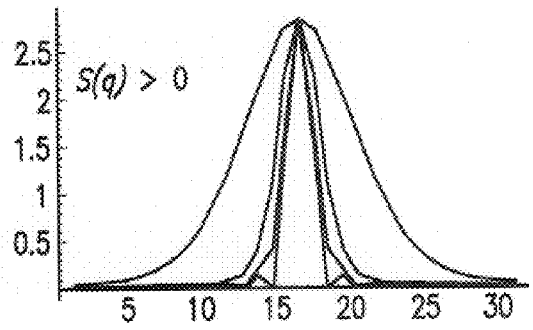
FIG. 4C SIMULATED EFFECT OF CYCLIC STRAIN ON THE DIFFUSION SPECTRUM:
SHEET-SLIP CAUSES NON- GAUSSIAN DIFFUSION
SHEET THICKNESS:
0μ(CONTINUUM)    50μ    100μ    150μ
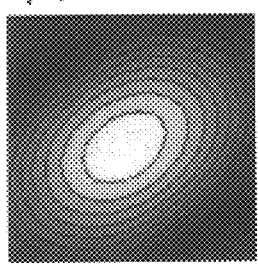 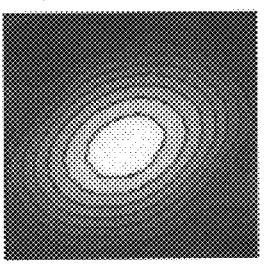 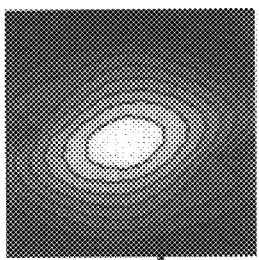 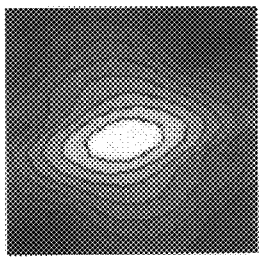
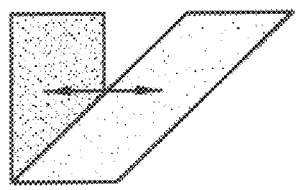
SHEET HALF-THICKNESS
EINSTEIN LENGTH AT
1 R-R INTERVAL
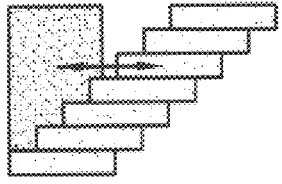
FIG. 10
CARDIAC DIFFUSION MRI *IN VIVO*
TWICE-GATED STIMULATED ECHO
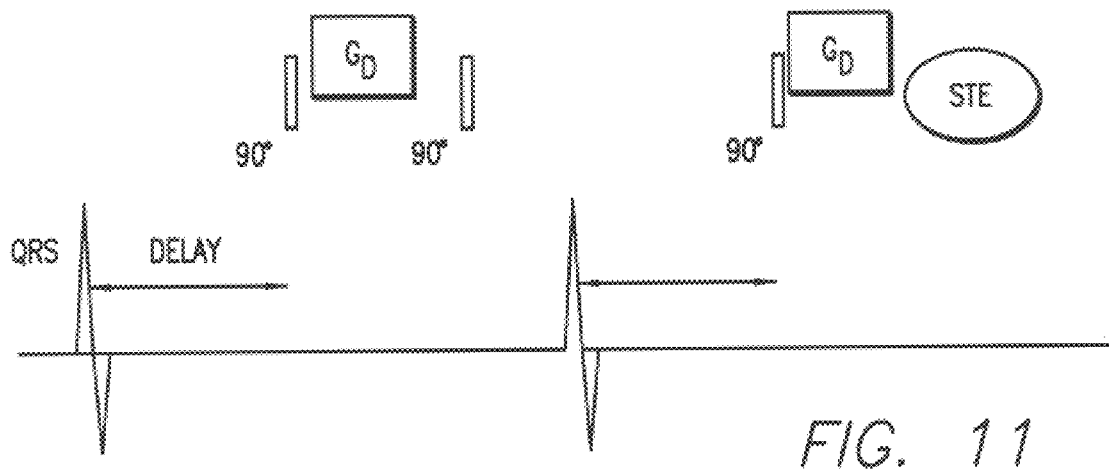
FIG. 11

HUMAN CARDIAC DIFFUSION SPECTRA IN VIVO, 60 μm STE

DIFFUSION IMAGING OF TISSUES

CROSS-REFERENCE TO RELATED APPLICATION

This application claims priority from U.S. Provisional patent application Ser. No. 60/193,938 filed on Mar. 31, 2000, which is incorporated herein by references in its entirety.

TECHNICAL FIELD

This invention relates to diffusion imaging of tissues.

BACKGROUND

In the past decade, magnetic resonance imaging (MRI) methods have been developed that by mapping the diffusion tensor of tissue water can nondestructively map the structural anisotropy of fibrous tissues in living systems. Recently, these methods have been used to elucidate fiber architecture and functional dynamics of the myocardium and of skeletal muscle, and used in the nervous system to identify and map the trajectories of neural white matter tracts and infer neuroanatomic connectivity.

Notwithstanding this progress, the diffusion tensor paradigm has limitations. Because MRI spatial resolution typically is far in excess of the diffusion scale, each resolution element (voxel) represents the summed signal of distinct diffusional environments, which is generally under-specified by the six degrees of freedom of the diffusion tensor.

SUMMARY

The invention relates to the use of diffusion spectrum MRI to map complex fiber architectures or structures in tissues with a high level of resolution. The new methods resolve intravoxel heterogeneity of diffusion in vivo with MRI of diffusion density spectra.

In general, the invention features a method of constructing an image representative of structure within a tissue, by (a) inducing a population of spins in the tissue to produce a set of nuclear magnetic resonance (NMR) signals, wherein the set comprises a family of complex Fourier-encodings of a distribution of three-dimensional displacements of the spins in the population; (b) converting each of the NMR signals in the family of complex Fourier-encodings into a positive number to form a family of positive numbers; (c) reconstructing from the family of positive numbers a function that approximates the distribution of three-dimensional displacements of the spins in the population; and (d) constructing an image that represents the function, whereby the image represents structure within the tissue.

In this method, each spin in the population can be within a three-dimensional voxel, and the population of spins can be induced to produce the set of NMR signals by the application of a set of magnetic gradient pulses, e.g., applied in a pulse train whose time-intensity integral is zero. The pulses in the pulse train can be bipolar gradient pulses, and the gradient pulses can be transected by one or more 180° radio frequency (RF) pulses and the gradient sign can be reversed following each 180° pulse. The NMR signals can also be converted into positive numbers by determining the modulus ($z \to |z|$), or by determining the squared modulus ($z \to zz^*$).

In the new methods, the function can reconstructed by determining the discrete Fourier transform, or by interpolation and regridding, followed by determining the discrete Fourier transform. In some embodiments, the new methods can be performed for multiple contiguous locations in the tissue, and then followed by further constructing a curve that represents fiber tracts in the tissue that conform to the orientation of directions of maximum displacement.

In some embodiments, the image is a three-dimensional graphic image, e.g., that represents the three-dimensional distribution of spin displacement for a voxel. The graphic image can also be a three-dimensional polar plot of the amplitude of spin displacement in multiple directions, and the polar plot can be colored to represent the amplitude and orientation of spin displacement. For example, the color can be coded to assign red, green, and blue to the amplitude of spin displacement in each of three orthogonal coordinates. The amplitude of spin displacement is the relative probability of spins displacing a constant distance in any direction.

The graphic image can also be a density plot of the spin density in a position-angle space, e.g., a slice or projection through a 6-dimenional position-angle space.

In these methods the tissue is a heterogeneous tissue, e.g., a tissue with two or more tissue types. The tissue can be brain tissue, e.g., neural white matter, that may have, for example, multiple fiber orientations. The tissue can also comprise normal and pathologic tissue, and the pathologic tissue can be cerebral edema, cerebral hematoma, cerebral neoplasm, cerebral metastasis, or ischemic tissue. The pathologic tissue can also comprise a neurodegenerative disease, such as Huntington's chorea, multiple sclerosis, or stroke. The tissue can also be muscle, such as heart or tongue.

In another embodiment, the new methods can be used to diagnose a disorder in a tissue, such as brain or heart using the image. In other embodiments, the methods can be used to construct a model of fiber tracts in the brain based on the image or to map a surgical site in the tissue, e.g., the brain or heart, using the image. The image can be combined with images of other magnetic resonance imaging (MRI) contrast parameters, such as NMR contrast parameters, e.g., T1, T2, magnetization transfer contrast (MTC), or blood oxygen level dependent contrast (BOLD).

In yet another embodiment, the invention includes a computer-implemented program for constructing an image representative of structure within a tissue, the program comprising a plurality of program instructions stored on a electronic apparatus-readable medium for implementing the steps of: (a) inducing a population of spins in the tissue to produce a set of nuclear magnetic resonance (NMR) signals, wherein the set comprises a family of complex Fourier-encodings of a distribution of three-dimensional displacements of the spins in the population; (b) converting each of the NMR signals in the family of complex Fourier-encodings into a positive number to form a family of positive numbers; (c) reconstructing from the family of positive numbers a function that approximates the distribution of three-dimensional displacements of the spins in the population; and (d) constructing an image that represents the function, whereby the image represents structure within the tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

The file of this patent contains at least one drawing executed in color. Copies of this patent with color drawings will be provided by the Patent and Trademark Office upon request and payment of the necessary fee.

FIGS. 1A and 1B are representations of a diffusion contrast image of signal (q) and the corresponding displacement (or diffusion) spectrum (r) resulting from a three-dimensional Fourier transform of diffusion contrast image.

FIG. 2 is an overview of the new diffusion spectrum MRI method.

FIG. 3 is a schematic overview of a "balanced" diffusion pulse sequence technique that can be used to image tissue in vivo.

FIGS. 4A to 4C are representations of diffusion images in a one-dimensional box. The two graphs show corresponding displacement spectra (4B) and their Fourier transforms (4C).

FIG. 10 is a schematic diagram of a simulated effect of cyclic strain on a diffusion spectrum of cardiac muscle, caused by the sheet-like arrangement of fibers in cardiac muscle.

FIG. 11 is a schematic overview of a twice-gated stimulated echo technique that can be used to image cardiac tissue in vivo.

DETAILED DESCRIPTION

Figure 5A:
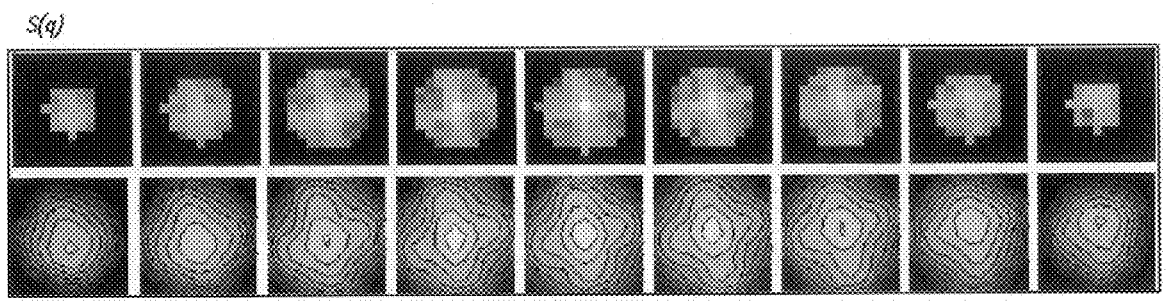
FIGS. 5A and 5B are representations of raw MR image data, and a diffusion contrast image for one voxel corresponding to brain tissue, respectively.

The invention relates to methods to image and map complex fiber architectures in tissues such as the brain, heart, tongue, and skeletal muscle with a high level of resolution. The new methods provide far greater resolution and information than standard MRI methods.

The invention provides methods to map complex tissue fiber architectures using MRI of the three-dimensional diffusion spectrum (q-space imaging). Three-dimensional spectra of spin displacements are phase-encoded and reconstructed by use of a Fourier transform of the modulus of the detected complex signal; the modulus is used to exclude effects of organ motion, but as shown herein, without loss of significant information. Diffusion imaging studies of cardiac and lingual tissue demonstrate spectral patterns of local dispersion of fiber orientations and local intersection of fiber populations, details of fiber architecture not previously identified by noninvasive means. In normal human subjects, diffusion spectroscopy resolves intravoxel heterogeneity of diffusion anisotropy in cerebral white matter. Orientational maxima of the diffusion spectrum directly resolve the orientations of known cerebral white matter tracts, in regions of simple unidirectional fiber architecture, and also in tract intersections, where the orientations of major tracts incident on a particular location correspond to multiple maxima of the 3-D diffusion spectrum.

The new methods allow the imaging of more than one tissue type with much higher resolution than previously possible. The two or more tissue types can differ in fiber orientation, e.g., different fiber bundles in the brain or muscle fibers, e.g., in the tongue or heart. The two or more tissue types can also differ in composition, e.g., healthy compared to cancerous tissue, or any tissue compared to a pool of blood or fluid (edema) or clot of blood (embolus). In some embodiments, the different tissue types can be distinguished if they have different $T_1$, or $T_2$ characteristics, e.g., if a patient has a stroke and certain bundles of brain tissue start to become necrotic, the necrotic tissue can be distinguished from normal healthy tissue.

General Methodology

The basic steps of the new methods include acquiring data (a set of signals) from multiple locations in a sample of tissue (e.g., in a 3-Ddimensional set) to generate diffusion spectra based on differences of diffusion of matter in each location or voxel in a three-dimensional set of locations. The first step is carried out using standard diffusion-sensitive MRI techniques and devices. Next the diffusion spectra are reconstructed by taking the Fourier transform of the sets of data to obtain displacement spectra that are representative of the structure with the tissue sample. In a subsequent step, the displacement spectra can be rendered in a 3-D graphical representation.

More specifically, spectra of spin displacements are phase-encoded with a conventional suite of motion-sensitizing magnetic gradient pulses using known techniques, and are reconstructed by Fourier transformation of the complex signal (set of signals), or the modulus of the complex signal. The use of the modulus of the signal is useful for the present methods and the rationale for its use has two parts. First, the signal modulus excludes phase errors related to tissue motion, e.g., brain motion due to arterial pulsation or cardiac tissue motion due to the heartbeat. Second, the signal modulus is sufficient to accurately specify diffusion spectra of tissue, such spectra belonging to the class of functions whose Fourier transforms are real and positive, which is demonstrated as follows.

In an idealized case, if a voxel consisted of noninteracting anisotropic microenvironments, its net signal would be a sum of Gaussians and as a result would be positive, as required in the new methods. In a realistic case, however, one must allow for restriction and exchange. Accordingly, each voxel is modeled as a heterogeneous network of microenvironments between which there is random spin exchange: compartments i∈I, wherein I is an index set, with exchange governed by a matrix M, where $M_{ij}$ is the probability of spin exchange between compartments i and j per unit time. Note that diffusion anisotropy is not a primary feature of this model, but can enter secondarily through orientational differences in rates of exchange between compartments.

By selecting compartments of equal spin content, the rate of spin flux due to spin exchange is proportional to L=M−1 where 1 is the identity, and its net transport after time τ is given by the matrix exponential $$P_\tau = \exp(\tau L) \quad [1]$$

Denoting the three-dimensional (3-D) location of the i-th compartment by x(i), then displacements between compartments are parametrized by r=x(i)−x(j), and the spectral density of such displacements is the ensemble sum $$P_\tau(r) = \Sigma ij \text{ such that } x(i)-x(j)=r, P_{\tau;\ ij} \quad [2]$$

The Fourier transform of this displacement spectrum is $$c^{-1} S_\tau(q) = \sum_r P_\tau(r) \exp(\sqrt{-1} qr) \quad [3]$$
$$= \sum_{ij} P_{\tau;ij} \exp(\sqrt{-1} q(x(i)-x(j)))$$
$$= f_q * P_\tau f_q$$

where c is a constant, q is the transform coordinate dual to r, $f_q$ is the vector $$f_q = \{\exp(\sqrt{-1} q\ x(i))\}\ i\in I$$

where * is the Hermetian conjugate.

We now introduce the assumption that flux asymmetries between compartments are insignificant, so that rates of exchange are symmetrical $$M = M^T \quad [4]$$

Then the eigenvalues of M are real, and so those of $P_\tau$ are real and positive by the spectral mapping theorem, whence $S_\tau(q) = f_q^* P_\tau f_q$ is real and positive and $$S_\tau(q) = |S_\tau(q)| \quad [5]$$

It follows that any phase observed in the signal must have a source other than such diffusion, and the spectrum of displacements $P_\tau(r)$ is accurately reconstructed as the Fourier transform of the modulus $|S_\tau(q)|$, as expressed by the Fourier-transform pairing $$P_\tau(r) \leftrightarrows |S_\tau(q)| \quad [6]$$

Note that this spectrum $P_\tau(r)$ corresponds to the flux of spin signal rather than of spin density, and so $P_\tau(r)$ cannot be equated with the average of diffusion probability density functions (PDF's). Note too that there is no implication that the displacement spectrum of spins of a particular starting compartment has a positive transform; such positivity only emerges after the ensemble sum over all compartments in Eqs. 2–3.

FIGS. 1A and B show the general application of the new methods. In FIG. 1A, signal (q) of two fibers within a single 3-D cubic location or voxel of tissue are represented by two diffusion contrast images at right angles to each other. The resulting combined image representing the content of one voxel of tissue is a non-descript shape. On the other hand, when the 3-D Fourier transform of the diffusion contrast are taken to provide the corresponding diffusion spectra, shown in FIG. 1B, the resulting 3-D shapes of the combined spectra present a much more detailed and accurate view of the two crossing fibers, and the resulting 3-D image provides a more detailed and informative representation of the voxel. In one specific embodiment, the new method uses a single-shot spin echo in Echo Planar Imaging (EPI) with extra 180° RF pulses to "balance" diffusion-gradient eddy effects at a resolution of $3^3$ to $4^3$ mm$^3$. Although a single shot technique must be used in the new methods, techniques other than EPI can be used, such as, for example, line scanning. For phase-encoded diffusion, we used about 500 "bipolar" gradients in a 3-D lattice in a spherical keyhole with $|q|^\leq$ constant and $b_{max}$=20,000 s mm$^{-2}$. In the next step, the diffusion spectrum at each voxel is reconstructed as the 3-D Fourier transform of the signal modules P(r)=F/s(q)/.

FIG. 3 shows a description of a "balanced" diffusion pulse sequence in which the balanced diffusion pulse sequence is a symmetric spin echo that fills available TE with gradients and cancels residual eddys with "+" and "−" gradient transitions.

FIGS. 4A to 4C provide an example of diffusion restricted in a 1-dimensional (1-D) box. The figures in FIG. 4A show contours over time. The two graphs in FIGS. 4B and 4C show the corresponding displacement spectra (P(r)) and their FTs over time (S(q)>0). The different curves of the graphs represent measurements at discrete time points (10, 30, 50, 70, and 90, in arbitrary units used in this numerical simulation).

The new methods can be applied not only to data in 3-D, but in 2-D as well. In addition, the sampling need not be linear. For example, one can sample non-uniformly in K-space.

Applications

The new methods can be used to accurately image various tissues, including brain, cardiac, and muscle, such as skeletal muscle, tissues and in particular can resolve pluralities of tissue types with high resolution as described above. For example, the new methods can be used to carefully analyze the white matter of the brain, and to diagnose disorders of the brain, for example disorders that affect the white matter, such as demyelinating diseases, e.g., multiple sclerosis. Other brain disorders such as head trauma, e.g., with diffuse axonal injury, and stroke can also be imaged and diagnosed. In addition, the new methods can be used to help a surgeon to visualize and map a surgical site, e.g., in the brain. Other disorders that affect the brain, such as dyslexia and schizophrenia, can also be analyzed.

In the heart, the new methods provide a new way to image the motion of the cardiac muscle, e.g., to characterize myocardial tissue dynamics, or to diagnose disorders, such as diastolic dysfunction and fibrosis of the heart muscle. In addition, the new methods may lead to ways to differentiate between benign and deadly myocardial hypertrophy. Tissues in other organs, such as the kidney, can also be imaged and analyzed.

The new methods can also be applied to accurately map the fibers in the brain that form bundles or tracts of fibers, in a field known as tractography. To a considerable extent, interest in mapping cerebral white matter orientations is prompted by the promise of cerebral tractography, the mapping of neuroanatomic connectivity, here to be done noninvasively by finding families of curves that best fit the observed fields of fiber orientations. Diffusion spectroscopy relies upon the orientational coherence of fibers within a voxel and identifies fiber orientations as maxima of the diffusion spectrum. Such maxima occur whenever a sub-population of fibers at a location has high orientational coherence. As a result, the spectroscopic approach significantly uncouples the detectability of fiber orientations from partial volume effects. A principal function of spatial resolution in diffusion spectroscopy is to overcome orientational dispersion within each fiber tract.

Particular methods of data analysis and procedures to augment diffusion spectroscopy imaging (DSI) contrast will be appropriate to specific disease categories and diagnostic questions. In conditions associated with antegrade or retrograde degeneration of specific white matter tracts, including stroke, MS, post-operative change and Huntington's disease, it is possible to map the T1, T2 and MTC of the diffusion spectra to precisely define the parts of the spectra that are associated with the pathologic process. Isolation of spectral components in this way will be useful to quantify the extent and severity of pathologic involvement. Delineation of the extent of edema will be possible based on the relative intensity of directionally isotropic components of the diffusion spectra or of components with long T2. Presence of hematoma may be defined by T2* maps of the diffusion spectra. Fiber mapping will be of value in preoperative planning, to define important white matter pathways, and so to help minimize operative damage to them. By enabling signal characteristics, including diffusion anisotropy and the conventional MRI parameters (e.g., T1, T2, MTC), of individual neural fiber tracts to be resolved with reduced contamination by intersecting tracts, diffusion spectrum MRI will improve the sensitivity and specificity of present diffusion tensor imaging for the diagnosis of schizophrenia, dyslexia, Alzheimer's disease, and other disorders that now rely on such measurements.

Primary measures of tract local dispersion are bend, twist, and splay, and these terms in general produce dispersion proportional to the linear resolution squared. These dispersive effects may explain the reduced discrimination in present images of subcortical white matter tracts, whose bending radii may be as small as the cortical thickness of 1–2 mm, and so should be imaged with spatial resolution no greater than this value, twice as fine as present resolution.

The diffusion model described herein has been constructed to include the possibility of free but incomplete exchange between distinct, possibly anisotropic, local microenvironments. This may be expected in interfacial zones between regions of contrasting diffusion, for example, where fiber bundles intersect or permeate more isotropic tissue. Free and restricted diffusion represent exemplary limiting cases of this model. Spatially homogeneous diffusion represents a spatial convolution, and so its displacements are a Levy function, i.e., a function that is stable under self-convolution, whose Fourier transform is stable under self-multiplication, and is thus positive. This corresponds to the case where few spins interact with a boundary, and so describes the limit as $\tau \to 0$. In fully restricted diffusion ($\tau \to \infty$) the displacement spectrum tends to the autocorrelation of the restriction geometry, a function whose Fourier transform again is positive. The operator $L=M-1$ can be considered a Laplacian on the network of interconnected compartments, with diffusion, as usual, its exponential.

Like all diffusion MRI in vivo, the present methods are vulnerable to artifacts related to non-diffusional motion. Macroscopic motion may contaminate diffusion contrast when it produces local signal loss due to intra-voxel velocity gradients, but such effects are readily recognized in the phase of the images. Residual errors also may arise from other forms of spin flux including nonrandom flow of tissue water related to perfusion. For example, one can square the data to obtain the autocorrelation of the probability density function (PDF).

In present studies, resolution and field-of-view of the spectral dimensions were selected to accommodate the known range of diffusivities in cerebral white matter, $10^{-2}$–$10^{-3}$ mm$^2$s$^{-1}$. By the Nyquest criterion, this range should be sampled using a grid of at least 10–20 samples in radius, and failure to achieve this may lead to aliasing and truncation artifacts. While such are not readily evident in the present studies, this may reflect present signal to noise ratios. Conversely, the number of samples in present diffusion encodings seems far in excess of the few dozen degrees of freedom that may be sufficient to describe the observed patterns of local diffusion, which suggests that more economical encoding strategies can be used. For example, one could sample a 3-D spherical shell and fill in the interior by extrapolation rather than sampling the complete 3-D solid sphere.

As noted, the present images of the diffusion spectrum reflect signal flux rather than mass flux and are weighted according to the contrast of the native images. As present studies are strongly T$_2$-weighted, their spectra principally show diffusion of long-T$_2$ species. Because this method is linear in signal in these examples, these spectra are transparent to other NMR contrast images and diffusion-resolved maps of relaxation times, magnetization transfer contrast, etc., could be straightforwardly obtained. For example, one can combine two 1-D data sets of different NMR parameters into one 2-D map, e.g., one could make a T$_1$ map of a diffusion spectrum using standard techniques. Such techniques may be useful to analyze tissue that has different NMR parameter characteristics. For example, one might image edema in the brain, where the edema has different T$_1$/T$_2$ characteristics than the brain tissue.

The ability of diffusion spectroscopy to resolve heterogeneous fiber orientation of cerebral white matter establishes that MRI voxels frequently encompass multiple diffusional microenvironments of distinct and contrasting orientation of anisotropy. From the perspective of diffusion spectroscopy, the model of diffusion as a tensor D asserts the Fourier duality $$\exp(-q*Dq) \Leftrightarrow \exp(-r*D^{-1}r) \qquad [7]$$

and in this sense a tensor model represents a second-order approximation to the diffusion spectrum. The effects of tissue heterogeneity upon the observed diffusion tensor can be directly assessed using present data. Tensor geometries have been described as oblate or prolate accordingly, as the two smaller or two larger eigenvalues have similar size, and prolate geometry correlated with intravoxel fiber orientations dispersion. When the map of tensor prolateness (difference of eigenvalues $D_2$–$D_3$) is compared with the map of tensor mistfit (mean squared difference between the diffusion spectrum and the tensor model), they are found to correlate with correlation coefficient r=0.75. This suggests that prolate geometry usually reflects a resolvable composite signal of heterogeneous tissue rather than a homogeneous microenvironment.

The new methods can be cascaded with any other NMR or MRI contrast method to obtain additional information.

Implementation

The invention can be implemented in hardware or software, or a combination of both. The invention can be implemented in computer programs using standard programming techniques following the method steps and figures disclosed herein. The programs should be designed to execute on programmable computers each including at least one processor, at least one data storage system (including volatile and non-volatile memory and/or storage elements), at least one input device, such as a keyboard, telephone, and at least one output device, such as a CRT, printer, or website. Program code is applied to input data to perform the functions described herein and generate output information, such as graphic images. The output information is applied to one or more output devices such as a printer, or a CRT or other monitor, or a web page on a computer monitor with access to a website.

Each program used in the new methods is preferably implemented in a high level procedural or object oriented programming language to communicate with a computer system. However, the programs can be implemented in assembly or machine language, if desired. In any case, the language can be a compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

EXAMPLES

The invention is further described in the following examples, which do not limit the scope of the invention described in the claims.

Example 1

Data were acquired from the brain of a normal human volunteer at 1.5 T using single-shot, echo-planar MRI acquisition, a spin-echo pulse sequence augmented by diffusion encoding gradient pulses, and by incorporating two 180° RF pulses to minimize eddy current effects. Imaging parameters included an isotropic spatial resolution of 2–4 mm, TE=176 ms, with diffusion mixing time $\Delta$=66 ms=$\tau$, encoding gradient pulse peak intensity $|G|_{max}$=40 mT m$^{-1}$ and effective duration $\delta$=60 ms, producing maximum spatial phase-modulation of $|q|_{max}$=0.63 radian $\mu^{-1}$, and a diffusion sensitivity of $b_{max}$=1.910$^4$ s mm$^{-2}$. In vivo acquisitions were synchronized with late diastole by a peripheral pulse trigger to minimize the effects of brain motion.

For each image plane, diffusion-weighted images were acquired for N=500 values of q-encoding (for each voxel; N can also be 100, 250, 400 or other numbers of values, and can be as small as 8 for 3-D and 4 for 2-D applications), comprising in q-space the points of a cubic lattice within the sphere of 5 lattice units in radius q, where $$q=(aq_x, bq_y, cq_z)\ 0.13\ \text{radian}\ \mu^{-1},\ a,\ b,\ c\ \text{integers},\ |(a,b,c)|\leq 5 \quad [8]$$

where the $q_i$ denote unit phase modulations in the respective coordinate direction. This encoding corresponds by Fourier transform to an isotropic 3-D spatial resolution of the displacement coordinate r of 10$\mu$ and an isotropic field of view of 50$\mu$.

Figure 5B:
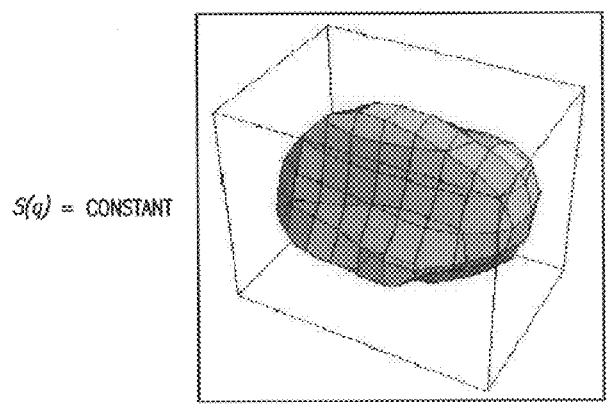

Data for one voxel are illustrated in FIGS. 5A and 5B; in this instance, the observed signal $|S_\tau(q)|$ is multi-modal resembling a tilted 'X', which indicates fibers of two orientations. FIG. 5A represents the actual raw data $|S_\tau(q)|$ represented as a set of contour plots for consecutive 2-D planes in q-space for one voxel (medulla). These data show an intensity maximum with the shape of a tilted 'X' the two lobes of which suggest contributions of two orientational fiber populations within this voxel. FIG. 5B represents a 3-D view with S(q)=constant, with 500 q-encodings, $|q|_{max}$=0.7 radian $\mu m^{-1}$, and $b_{max}$=20,000 s mm$^{-2}$.

Figure 6A:
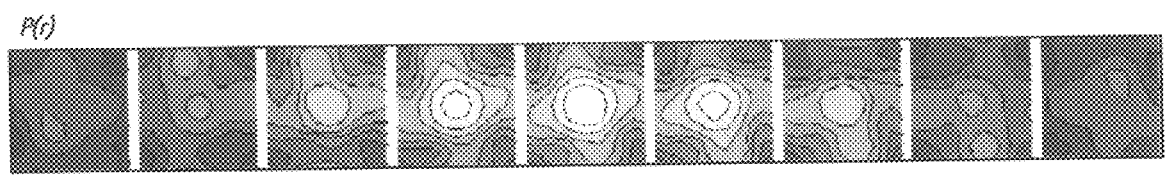
FIGS. 6A to 6C are representations of displacement (or diffusion) spectra and a polar plot (6C) generated by the new methods corresponding to the diffusion contrast images of FIGS. 5A and B.
Figure 6B:
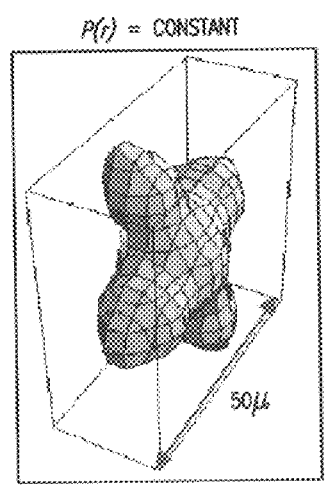
Figure 6C:
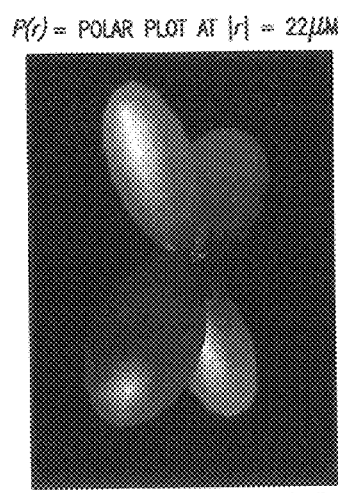

FIGS. 6A and 6B show the displacement density $P_\tau(r)$ reconstructed by a discrete 3-D Fourier transform of the data of FIGS. 5A and 5B represented by 2-D (FIG. 6A) and 3-D (FIG. 6B) contour plots, the latter a locus of points r such that $P_\tau(r)$=constant. The 3-D isotropic resolution was $2\pi/|q|_{max}$=9 $\mu$m. The 3-D displacement spectrum and especially the polar plot shows two well-defined orientational maxima as green and blue lobes (FIG. 6C). In FIGS. 5B and 6B and C, for each pixel measured values $|S_\tau(q)|$ were placed at the center of a cubical lattice, elements not sampled set to zero, and a diffusion spectrum $P_\tau(r)$ computed by 3-D discrete Fourier transform. FIG. 6A shows the reconstructed diffusion spectrum resulting from taking the Fourier transform of the diffusion contrast data of FIG. 5A, where $P_\tau(r)$ is represented by a 3-D contour plot (FIG. 6B) and a spherical polar plot (FIG. 6C). Orientational maxima are noted in directions that correspond to the two limbs of $|S_\tau(q)|$. Diffusion tensor fields were computed from these data by a linear least-squares fit.

At each pixel, a diffusion tensor D was computed from the overdetermined linear system $$\log(S)=c-bD \quad [9]$$

where $S=\{|S_\tau(q_i)|\}$ denotes the set of N signal amplitudes, c the unattenuated signal intensity, $b=(\Delta+\delta/3)q_i \otimes q_i$, the diffusion sensitivity matrix of dimension N×9, and D the diffusion tensor as a 9×1 vector. Eq. [9] in homogeneous form is $$\log(S)=\underline{b}(c, D) \quad [10]$$

where $\underline{b}=(1,-b)^T$ with $1=(1, \ldots, 1)^T$ of length N, which we solve for c and D $$(c, D)=\underline{b}^{-P}\log(S) \quad [11]$$

where $\underline{b}^{-P}=(\underline{b}^{T}\underline{b})^{-1}\underline{b}^T$ is the Moore-Penrose left pseudo-inverse. This avoids the asymmetric estimate c=log(S(0)), but estimates c using all available data.

Example 2

MRI of diffusion spectra were generated by the new methods for various tissues using the same imaging techniques described in Example 1. As a comparison, diffusion tensor images (DTIs) were also generated. In the following Figures, each rendered 3-D surface is a spherical polar plot of the values of P(r), a spherical surface whose radius at each orientation is determined by P(r) evaluated in this orientation at a constant displacement |r|–20 μ, with the dynamic range at each location linearly mapped to [0, 1].

Figure 7A:
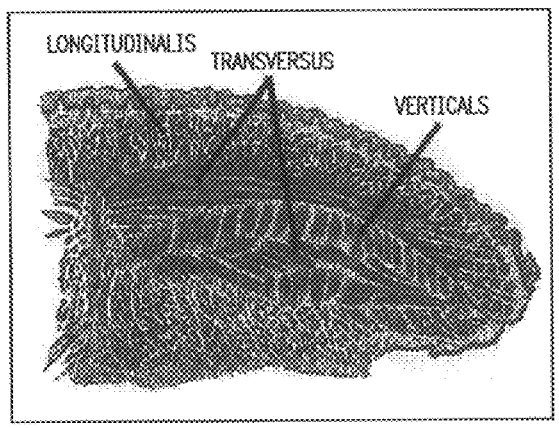
FIGS. 7A and 7B are a pair of schematic diagrams of a longitudinal-section and cross-section of a bovine tongue, respectively.
Figure 7B:
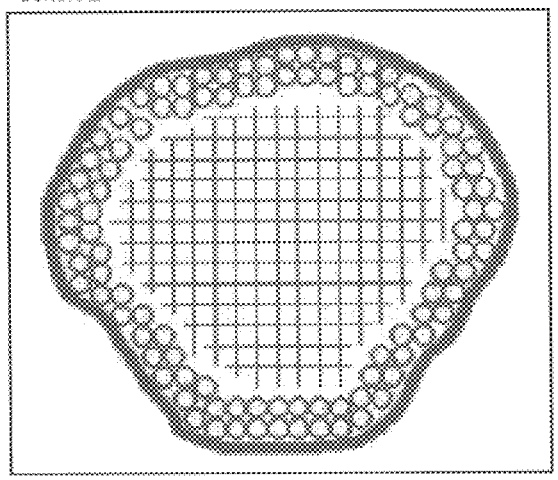
Figure 8:
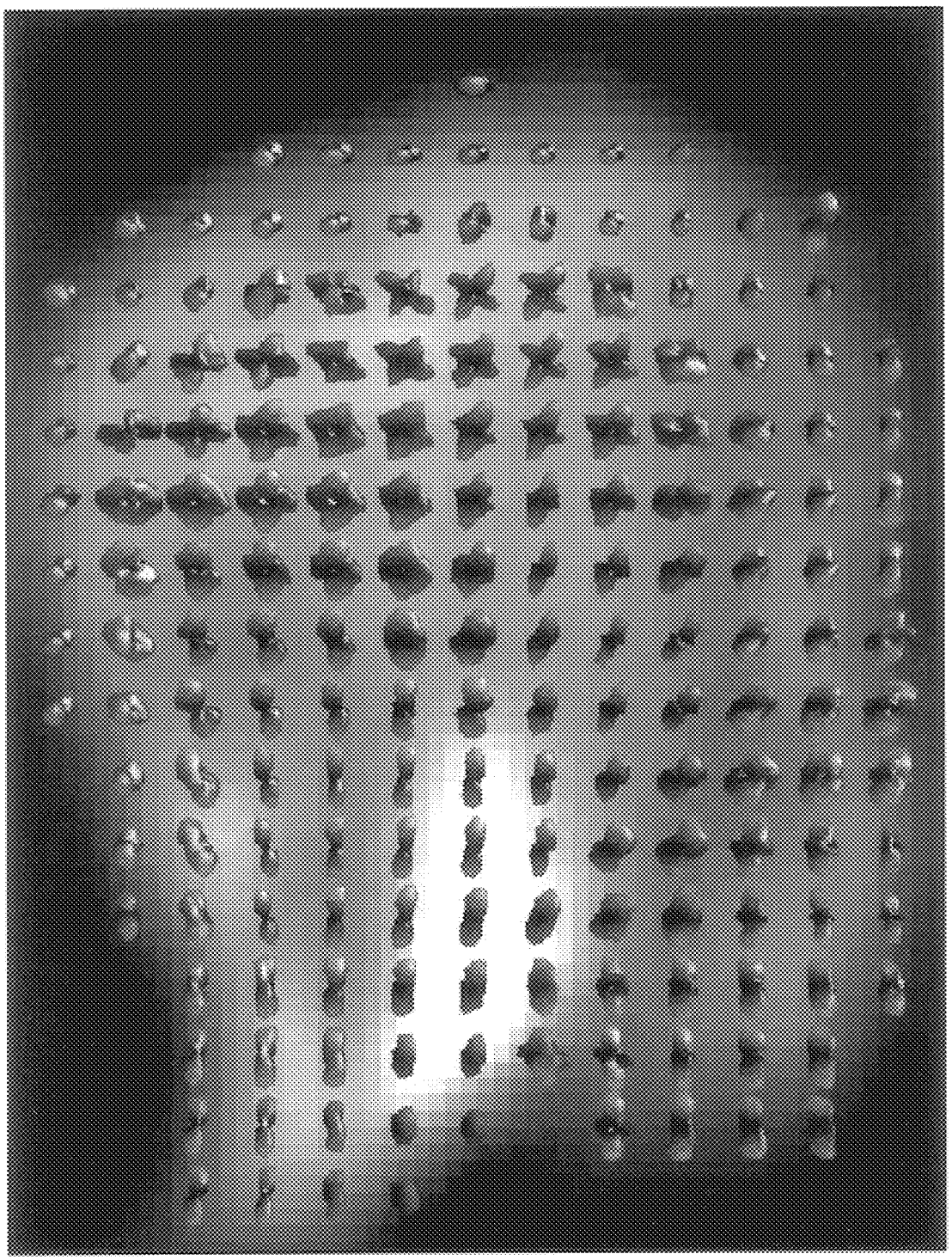
FIG. 8 is a representation of displacement spectra generated by the new methods of a cross-section of a bovine tongue.

As a simple example of fiber intersection, diffusion spectrum MRI were acquired from a fresh specimen of bovine tongue. As shown in FIGS. 7A and B, the intrinsic muscles of the tongue comprise a core and a sheath, wherein the sheath is a conventional skeletal muscle of longitudinal orientation, and the core is a specialized structure of crossing fiber bundles of the orthogonal transversus and verticalis muscles, a muscular hydrostat that by joint contraction of orthogonal elements lets the tongue stiffen, deviate, and protrude. As shown in FIG. 8, this architecture is clearly delineated by MRI of the diffusion spectrum. FIG. 8 shows that peripheral voxels have spectra with single, longitudinal maxima, while core voxels have spectra of two orientation maxima that are nearly orthogonal and parallel, and close to the plane of section.

Example 3

Figure 9:
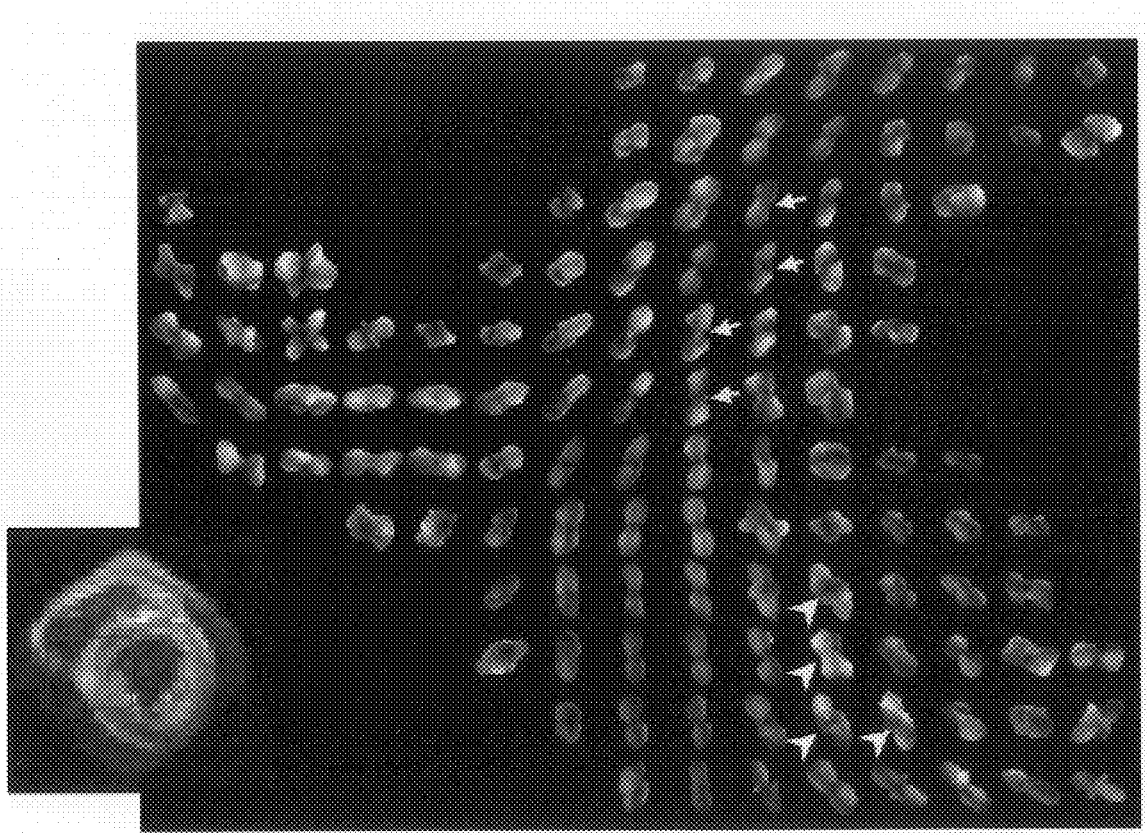
FIG. 9 is a representation of displacement spectra generated by the new methods of a left ventricle of a bovine heart.

Diffusion spectrum MRI of the bovine heart is shown in FIG. 9, illustrating the effects of continuous variation of tissue orientation. Myocardial fiber orientations lie along concentric helices about the ventricular circumferences whose angles of inclination, helix angles, have a smooth and monotonic variation from the inner to the outer wall. Diffusion spectra, like the diffusion tensor, illustrate this basic architecture, but also show cross-fiber anisotropies of two distinct types. First, a direction of minimal diffusion, or greatest restriction, is discerned, that, corresponding to the smallest eigenvector of the diffusion tensor, may be identified with the normal to the myocardial sheets. Second, the direction of maximum diffusivity is itself anisotropic, being broadened in the axial direction that is the orientation of maximum intravoxel dispersion of fiber angles due to the dispersion of fiber helix angles within each voxel. Multipolar spectra seen near the insertion of the right ventricular wall may reflect local mixing of left and right vetricular fiber populations.

FIG. 10 illustrates how the new methods can be used to analyze the motion of fiber bundles of the myocardium, which are organized into sheet-like packets.

FIG. 11 illustrates in schematic form the application of the new methods to obtaining data from a beating heart. After a delay of from about 0 to 1 second after the QRS, an RF pulse is applied (at 90°), followed by a diffusion encoding gradient ($G_D$) with an amplitude of about 4 Gauss/cm, which is applied for a duration of about 15 milliseconds, followed by a second RF pulse (at 90°). After the next QRS and delay, a third RF pulse is applied, followed by a second $G_D$, followed by a stimulated echo (STE).

Figures 12A, 12B, 12C:
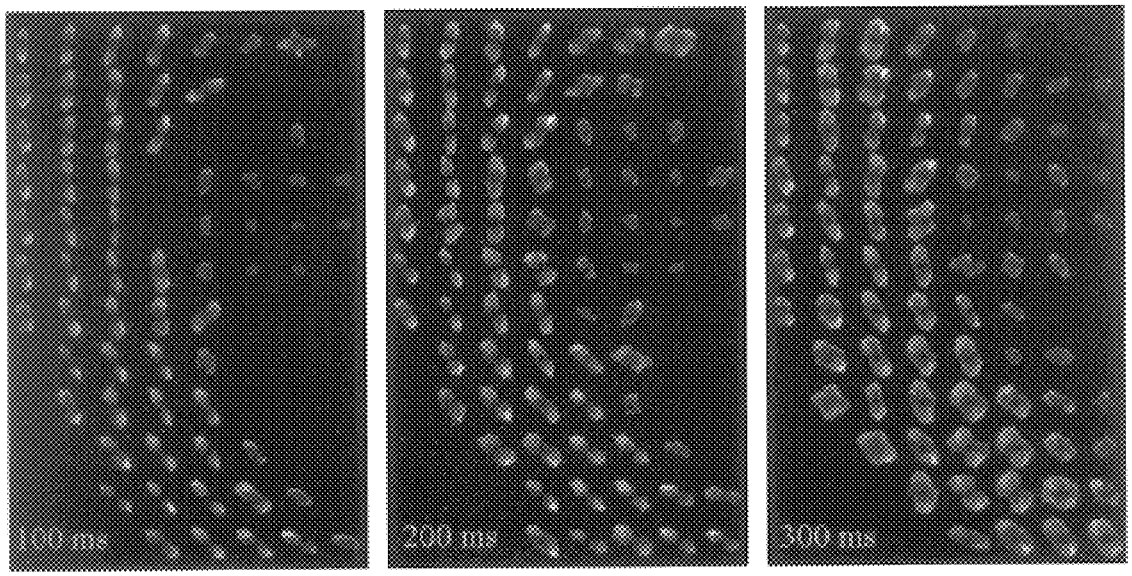
FIGS. 12A to 12C are a series of three representations of human cardiac displacement (diffusion) spectra generated by the new methods.

FIGS. 12A to 12C show three images of human cardiac diffusion spectra in vivo with a 60 micron STE, and GD having durations of 100, 200, and 300 ms.

Example 4

Figure 13:
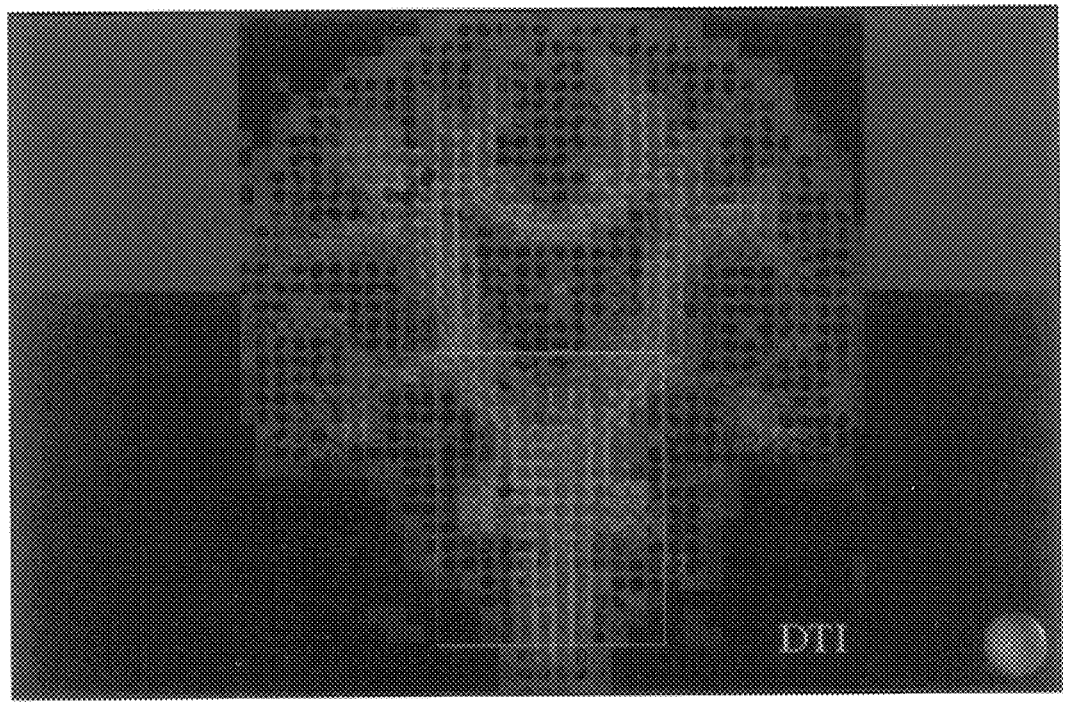
FIG. 13 is a representation of a diffusion tensor image (DTI) of brain tissue, showing rectangular 3-D voxels.
Figure 14:
FIG. 14 is a representation of diffusion spectra for the voxels in the white box inset of FIG. 13.
Figure 15:
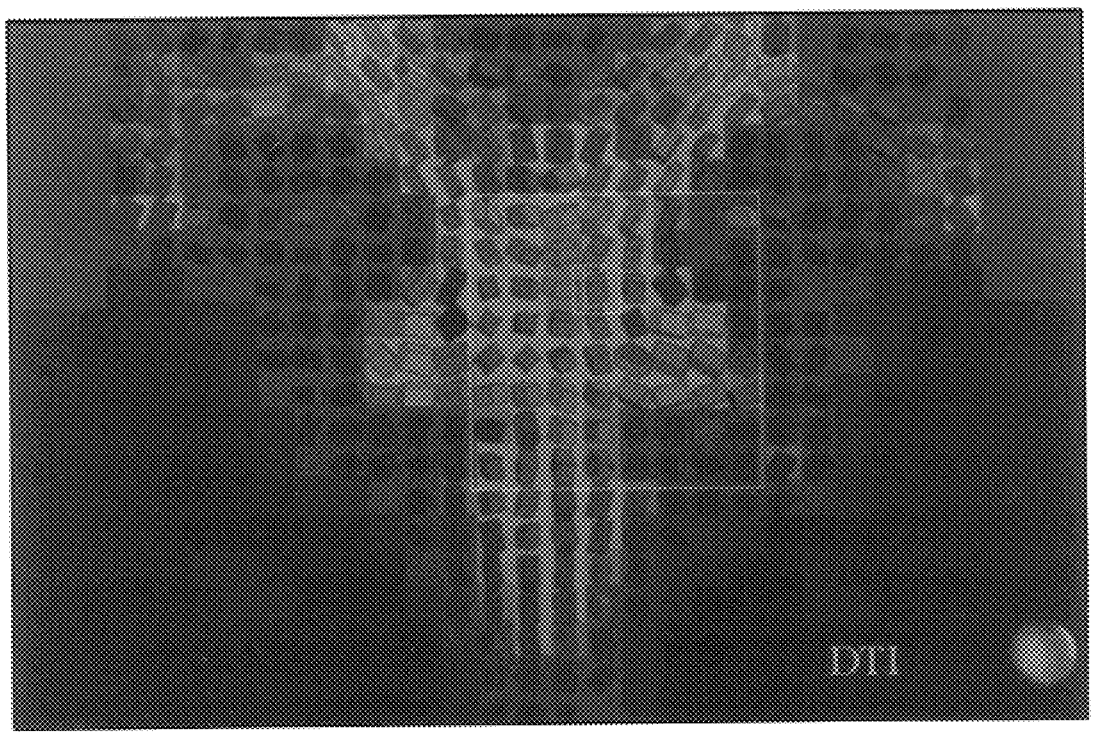
FIG. 15 is a close-up view of the DTI in FIG. 13.
Figure 16:
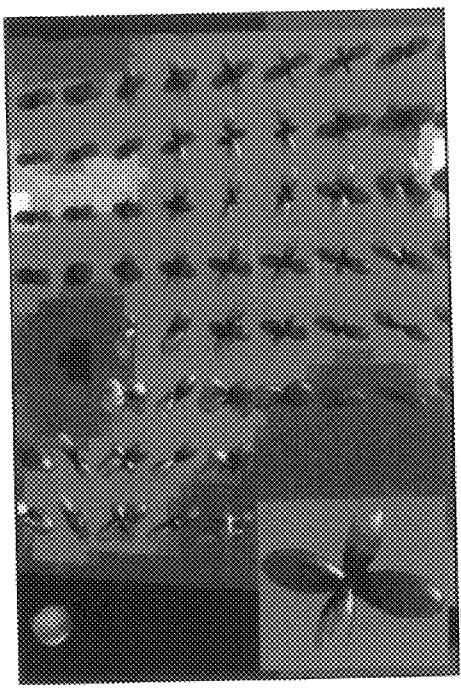
FIG. 16 is a representation of diffusion spectra for the voxels in the large white inset of FIG. 15, with a single voxel corresponding to the small white inset in FIG. 15.
Figure 17:
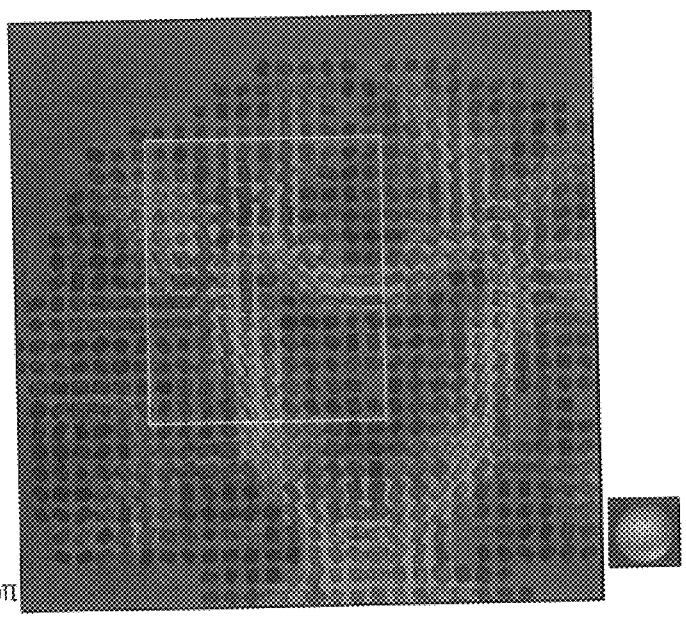
FIG. 17 is a representation of a DTI of another region of brain tissue, showing rectangular 3-D voxels.
Figure 18:
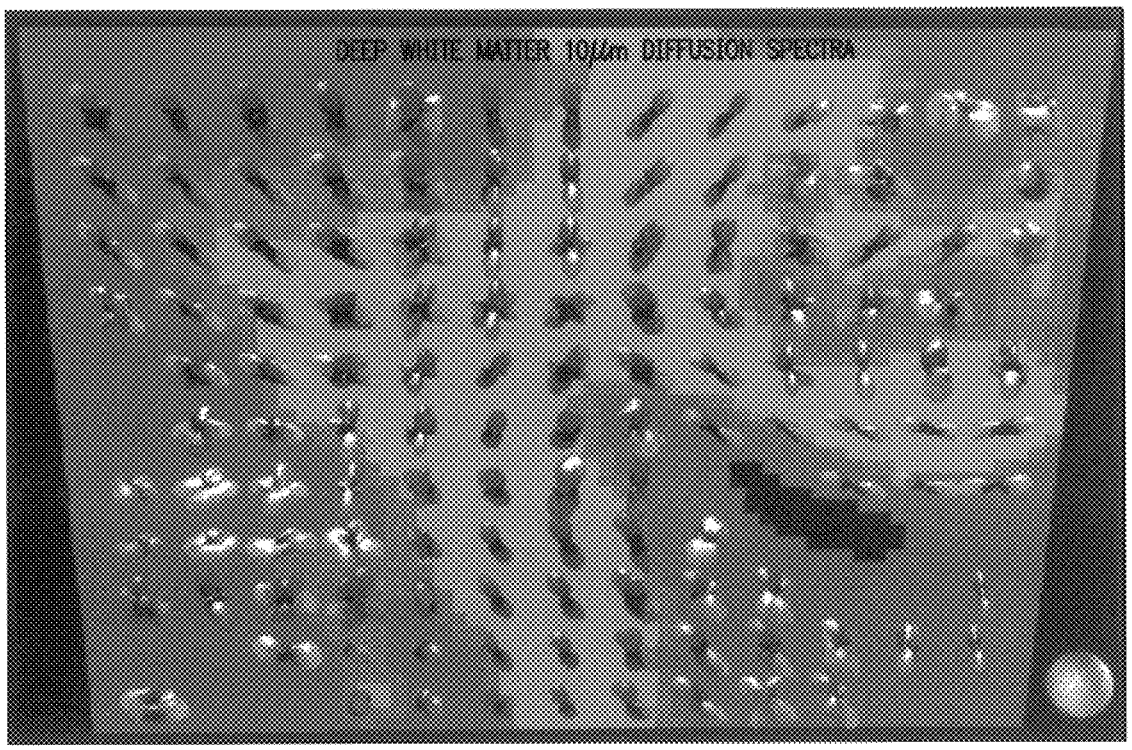
FIG. 18 is a representation of diffusion spectra generated by the new methods for the voxels in the white inset of FIG. 17.

Various diffusion tensor images (DTI) and various 3-D diffusion spectra for a coronal slice through the midbrain and corona radiata obtained from a normal volunteer are shown in FIGS. 13 to 21. FIG. 13 shows the diffusion tensor field for the entire slice; the value of the tensor at each pixel is represented by a rectangular box whose central axes represent the tensor eigensystem and whose color further codes the orientation of the leading diffusion eigenvector via the inset red-green-blue (R,G,B) code, and whose brightness represents the fractional anisotropy. FIG. 15 shows a close-up view of the DTI. FIGS. 14 and 16 are maps of 3-D diffusion spectra corresponding to the DTI of FIGS. 13 and 15, each local spectrum rendered as a 3-D spherical polar plot and colored via the mapping $\{|r|, |r_z|, |r_y|\} \rightarrow \{R,G,B\}$.

FIGS. 14 and 16 show the brainstem. In FIG. 16, orientational maxima of the diffusion spectra correspond to the axially orientated corticospinal tract (vertical; blue to blue-green) and the laterally orientated middle cerebellar peduncles (horizontal; green). Locations are seen where one orientation predominates or where both coexist, this taken to indicate presence of both tracts within the voxel. The inset detail in FIG. 16 shows the spectrum of one typical voxel that includes elements of both of these tracts as blue and green lobes.

Figures 19, 20:
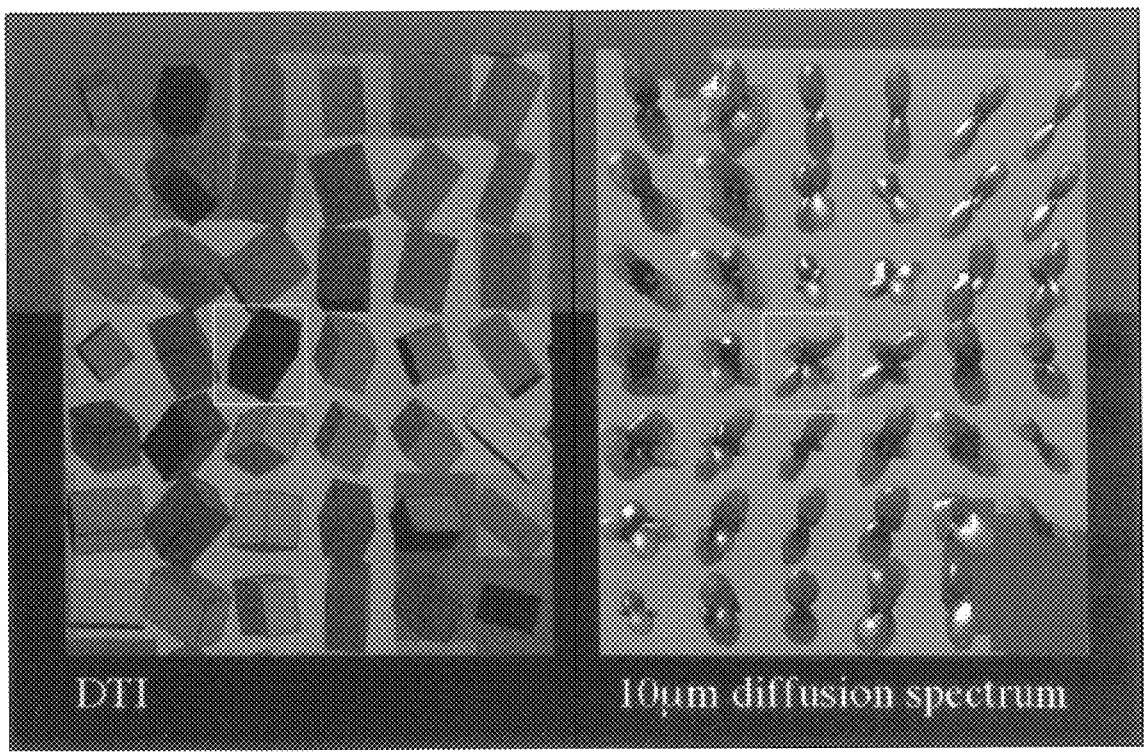
FIG. 19 is a close-up view of forty-two voxels in a DTI of deep white matter of brain tissue.
FIG. 20 is a close-up view of diffusion spectra generated by the new methods of the forty-two voxels in FIG. 19.
Figure 21:
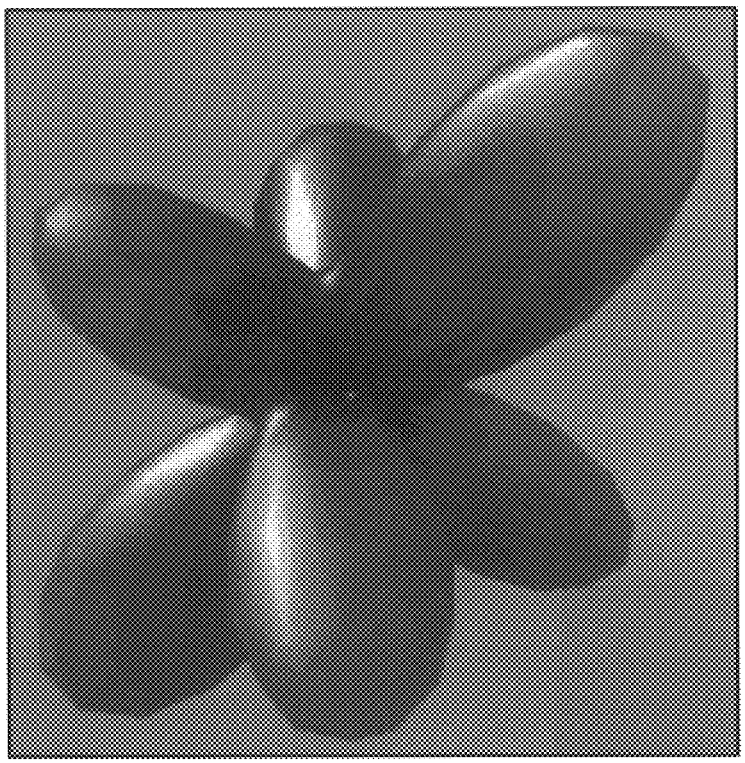
FIG. 21 is a further close-up of the diffusion spectra representing the voxel in the white inset in FIGS. 19 and 20.

FIGS. 17 and 19 and 18 and 20 show the deep white matter of the right cerebral hemisphere (DTI and diffusion spectra, respectively), including elements of the corpus callosum (green), corona radiata (blue) and superior longitudinal fasciculus (red). The inset in FIG. 20 shows the spectrum of a voxel with three-way intersection of these tracts, which can be seen in greater detail in the closer view shown in FIG. 21. Local spectra demonstrate tract intersections with 2 and 3 components. Note that the diffusion tensor that corresponds to the highlighted voxel of 3-way crossing corresponds to a diffusion tensor that is nearly isotropic. Diffusion spectra of voxels within sub cortical white matter have orientation maxima that generally appear less sharply defined than in the deep white matter, possibly related to more rapid spatial variation of fiber orientations.

Figure 22:
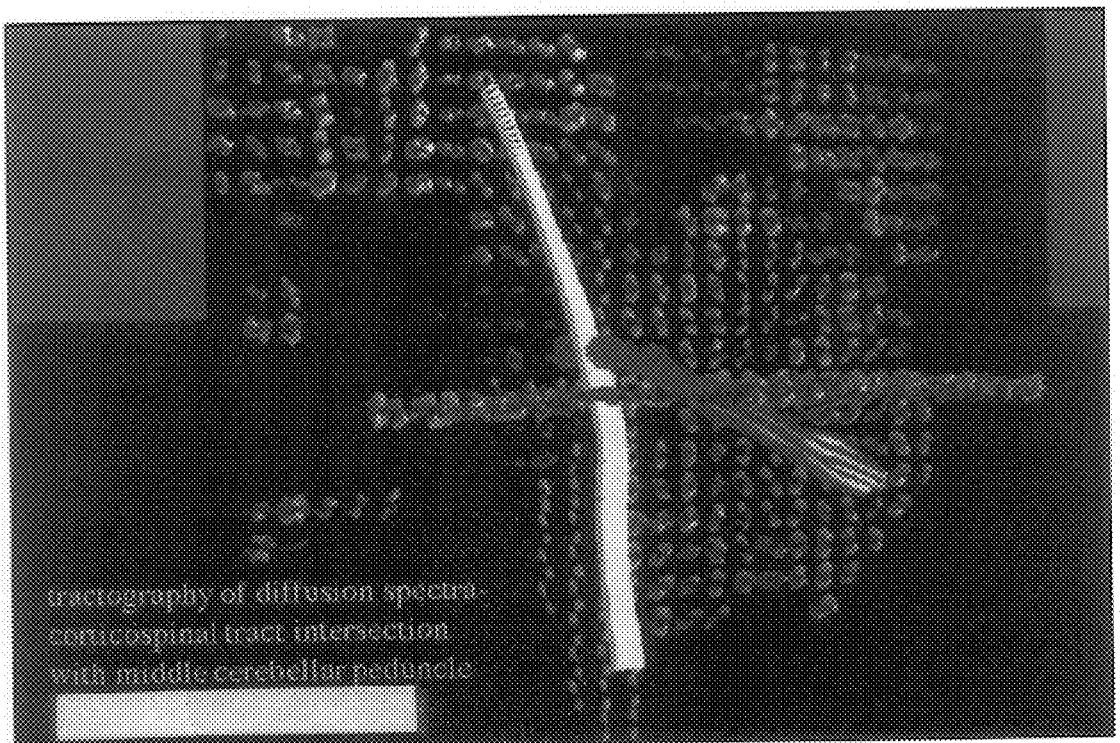
FIG. 22 is a series of diffusion spectra generated by the new methods overlaid with white and gray lines representing tracts of brain fibers (corticospinal tract and middle cerebellar peduncle, respectively) intersecting.
Figure 23:
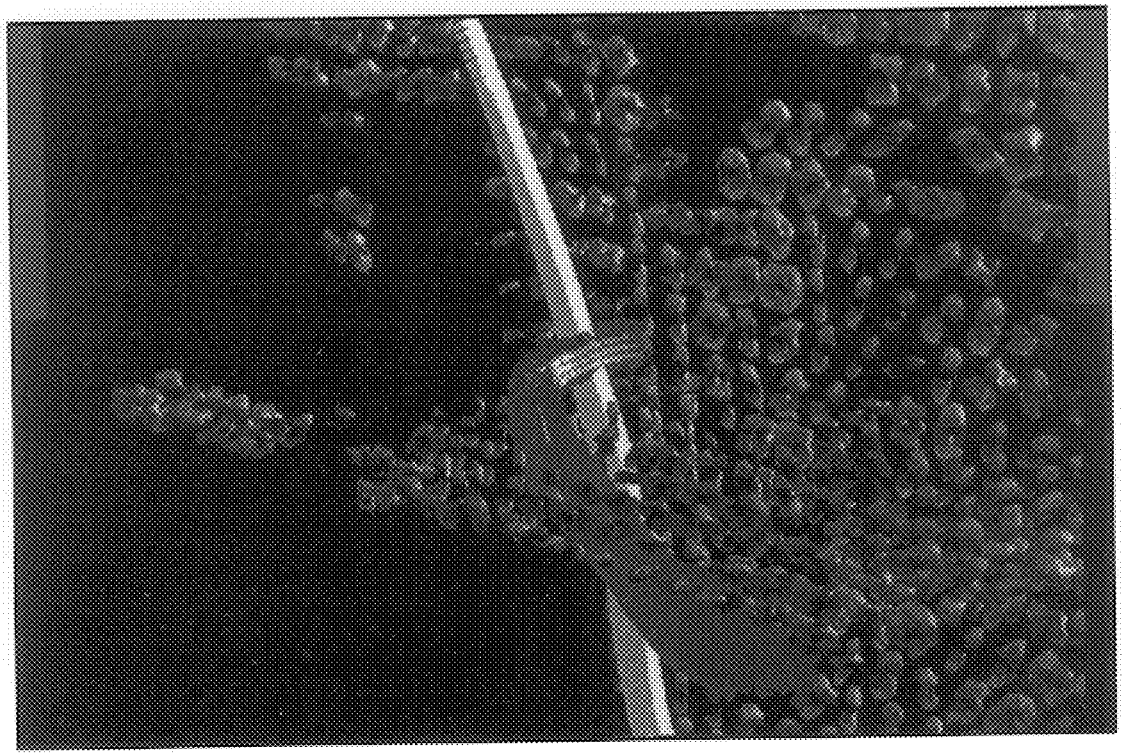
FIG. 23 is a close-up of the image in FIG. 22, and viewed from a different angle.

FIG. 22 shows the use of the new methods for tractography. FIG. 22 shows the intersection of the cortico spinal tract (indicated by a white band) with the middle cerebellar peduncle (gray band). FIG. 23 shows a close-up of FIG. 22 taken from another angle.

Other Embodiment

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of constructing an image representative of structure within a tissue, the method comprising
   (a) inducing a population of spins in the tissue to produce a set of nuclear magnetic resonance (NMR) signals, wherein the signals comprise a set of complex Fourier-encodings of a distribution of three-dimensional displacements of the spins in the population;
   (b) converting each of the NMR signals in the set of complex Fourier-encodings into a positive number to form a set of positive numbers to exclude phase information;
   (c) reconstructing from the set of positive numbers a function that approximates the distribution of three-dimensional displacements of the spins in the population in multiple directions; and (d) constructing an image that represents the function, whereby the image represents structure within the tissue.

2. The method of claim 1, wherein each spin in the population is within a three-dimensional voxel.

3. The method of claim 1, wherein the population of spins is induced to produce the set of NMR signals by the application of a set of magnetic gradient pulses.

4. The method of claim 3, wherein the magnetic gradient pulses are applied in a pulse train whose time-intensity integral is zero.

5. The method of claim 4, wherein the pulses in the pulse train are bipolar gradient pulses.

6. The method of claim 5, wherein the gradient pulses are transected by one or more 180° radio frequency (RF) pulses and wherein a gradient sign is reversed following each 180° pulse.

7. The method of claim 1, wherein the NMR signals are converted into positive numbers by determining the modulus ($z \rightarrow |z|$).

8. The method of claim 1, wherein the NMR signals are converted into positive numbers by determining the squared modulus ($z \rightarrow zz^*$).

9. The method of claim 1, wherein the function is reconstructed by determining the discrete Fourier transform.

10. The method of claim 1, wherein the function is reconstructed by interpolation and regridding followed by determining the discrete Fourier transform.

11. The method of claim 1, wherein the method is performed for multiple contiguous locations, and further constructing a curve that represents fiber tracts in the tissue that conform to the orientation of directions of maximum displacement.

12. The method of claim 1, wherein the image is a three-dimensional image.

13. The method of claim 12, wherein the three-dimensional image represents the three-dimensional distribution of spin displacement for a voxel.

14. The method of claim 12, wherein the image is a three-dimensional graphic of the amplitude of spin displacement in multiple directions.

15. The method of claim 12, wherein the polar plot is colored to represent the amplitude and orientation of spin displacement.

16. The method of claim 15, wherein the color is coded to assign red, green, and blue to the amplitude of spin displacement in each of three orthogonal coordinates.

17. The method of claim 16, wherein the amplitude of spin displacement is the relative probability of spins displacing a constant distance in any direction.

18. The method of claim 12, wherein the image is a density plot of the spin density in a position-angle space.

19. The method of claim 18, wherein the image is a slice through a position-angle space.

20. The method of claim 18, wherein the image is a projection through a position-angle space.

21. The method of claim 1, wherein the tissue is a heterogeneous tissue.

22. The method of claim 21, wherein the tissue is brain tissue.

23. The method of claim 22, wherein the tissue is neural white matter.

24. The method of claim 23, wherein the neural white matter has multiple fiber orientations.

25. The method of claim 21, wherein the tissue comprises normal and pathologic tissue.

26. The method of claim 25, wherein the pathologic tissue comprises cerebral edema, cerebral hematoma, cerebral neoplasm, cerebral metastasis, or ischemic tissue.

27. The method of claim 25, wherein the pathologic tissue comprises a neurodegenerative disease.

28. The method of claim 27, wherein the neurodegenerative disease is Huntington's chorea, multiple sclerosis, or stroke.

29. The method of claim 1, wherein the tissue is muscle.

30. The method of claim 29, wherein the muscle is heart or tongue.

31. The method of claim 1, further comprising diagnosing a disorder in a tissue using the image.

32. The method of claim 31, wherein the tissue is brain tissue.

33. The method of claim 32, further comprising constructing a model of fiber tracts in the brain based on the image.

34. The method of claim 1, further comprising mapping a surgical site in the tissue using the image.

35. The method of claim 34, wherein the surgical site is in the brain.

36. The method of claim 34, wherein the surgical site is in the heart.

37. The method of claim 1, further comprising combining the imaging method with one or more additional magnetic resonance imaging (MRI) contrast parameters.

38. The method of claim 37, wherein the contrast parameter is T1, T2, magnetization transfer contrast, or blood oxygen level dependent contrast (BOLD).

39. A computer-implemented program for constructing an image representative of structure within a tissue, the program comprising a plurality of program instructions stored on a electronic apparatus-readable medium for implementing the steps of:

(a) inducing a population of spins in the tissue to produce nuclear magnetic resonance (NMR) signals, wherein the signals comprise a set of complex Fourier-encodings of a distribution of three-dimensional displacements of the spins in the population;

(b) converting each of the NMR signals in the set of complex Fourier-encodings into a positive number to form a set of positive numbers to exclude phase information;

(c) reconstructing from the set of positive numbers a function that approximates the distribution of three-dimensional displacements of the spins in the population in multiple directions; and (d) constructing an image that represents the function, whereby the image represents structure within the tissue.

40. The method of claim 1, where the structure is one or more fiber orientations within the tissue.

41. The method of claim 14, wherein the graphic is a polar plot.

42. The method of claim 1, wherein the set of complex Fourier-encodings comprises a 3D grid.

43. The method of claim 1, wherein the set of complex Fourier-encodings comprises a 3D spherical shell.

* * * * *